(12) United States Patent
Okura et al.

(10) Patent No.: US 9,103,785 B2
(45) Date of Patent: Aug. 11, 2015

(54) METHOD AND APPARATUS FOR MELTING CURVE ANALYSIS OF NUCLEIC ACIDS IN MICROARRAY FORMAT

(75) Inventors: Michael Okura, Honolulu, HI (US); Bruce J. Richardson, Los Gatos, CA (US)

(73) Assignee: Emergence Genomics, LLC, Honolulu, HI (US)

( * ) Notice: Subject to any disclaimer, the term of this patent is extended or adjusted under 35 U.S.C. 154(b) by 885 days.

(21) Appl. No.: 13/001,036

(22) PCT Filed: Jun. 25, 2009

(86) PCT No.: PCT/US2009/048563
§ 371 (c)(1),
(2), (4) Date: Dec. 22, 2010

(87) PCT Pub. No.: WO2009/158451
PCT Pub. Date: Dec. 30, 2009

(65) Prior Publication Data
US 2011/0111968 A1    May 12, 2011

Related U.S. Application Data

(60) Provisional application No. 61/075,528, filed on Jun. 25, 2008.

(51) Int. Cl.
*G01N 21/64* (2006.01)
*C12Q 1/68* (2006.01)
(Continued)

(52) U.S. Cl.
CPC .............. *G01N 21/6408* (2013.01); *B01L 7/00* (2013.01); *G01N 21/6428* (2013.01);
(Continued)

(58) Field of Classification Search
CPC .............. G01N 21/6408; G01N 21/64; G01N 21/6428; G01N 21/6452; G01N 21/0332; G01N 2021/6441; C12Q 1/68; B01J 2219/00529; B01J 2219/00722; B01L 7/00; B01L 2100/0636; B01L 2300/0822; B01L 2300/088; B01L 2300/1838; B01L 2400/0487
See application file for complete search history.

(56) References Cited

U.S. PATENT DOCUMENTS

| | | |
|---|---|---|
| 2004/0091862 A1 | 5/2004 | Brandenburg et al. |
| 2004/0253624 A1 | 12/2004 | Smith et al. |

(Continued)

FOREIGN PATENT DOCUMENTS

| | | |
|---|---|---|
| EP | 1132485 A2 | 9/2001 |
| WO | WO9743611 A1 | 11/1997 |

OTHER PUBLICATIONS

Written Opinion, mailing date Oct. 19, 2009, for corresponding International Application No. PCT/US2009/048563.
First Office Action with English Translation, mailing date Oct. 10, 2012, for corresponding Chinese Application No. 200980124390.0.
International Search Report, mailing date Oct. 19, 2009, for corresponding International Application No. PCT/US2009/048563.
Extended European search report dated Apr. 3, 2013 for corresponding European Application No. 09 770 984.4.

*Primary Examiner* — Christopher M Babic
*Assistant Examiner* — Jeremy C Flinders
(74) *Attorney, Agent, or Firm* — Intellectual Property Law Group LLP

(57) ABSTRACT

A method and apparatus for performing melting curve analyses of nucleic acids on a microarray is described. The present method includes varying the temperature of a fluid on a microarray to dissociate and remove target DNA, scanning the mircoarray for fluorescence, collecting the target DNA removed from the microarray, and reusing the collected target DNA and the microarray. The apparatus of the present disclosure includes a microarray stage, a light source and detector, and a temperature controller, wherein the temperature controller is configured to adjust the temperature of a fluid within a sample chamber on the microarray such that the temperature of the fluid is varied during the analysis such that target DNA is dissociated from the microarray, and wherein the light source is directed to the microarray and the resulting fluorescence is perceived by the detector.

15 Claims, 11 Drawing Sheets

(51) Int. Cl.
    *B01L 7/00*   (2006.01)
    *C40B 60/12*   (2006.01)
    *G01N 21/03*   (2006.01)
(52) U.S. Cl.
    CPC .. *G01N 21/6452* (2013.01); *B01J 2219/00529* (2013.01); *B01J 2219/00722* (2013.01); *B01L 2300/0636* (2013.01); *B01L 2300/088* (2013.01); *B01L 2300/0822* (2013.01); *B01L 2300/1822* (2013.01); *B01L 2300/1838* (2013.01); *B01L 2400/0487* (2013.01); *C12Q 1/68* (2013.01); *G01N 21/0332* (2013.01); *G01N 2021/6441* (2013.01)

(56) References Cited

U.S. PATENT DOCUMENTS

2005/0239195 A1* 10/2005 Oram et al. ............... 435/288.3
2006/0281113 A1  12/2006 Church et al.
2007/0003958 A1   1/2007 Okamoto et al.

* cited by examiner

RELATIVE FLUORESCENCE

TEMPERATURE C

METHOD AND APPARATUS FOR MELTING CURVE ANALYSIS OF NUCLEIC ACIDS IN MICROARRAY FORMAT

CROSS-REFERENCE TO RELATED APPLICATIONS

This application is a U.S. National Phase application, under 35 U.S.C. §371, of International Application no. PCT/US2009/048563, with an international filing date of Jun. 25, 2009 and claims benefit of provisional U.S. Application No. 61/075,528 filed on Jun. 25, 2008, and which are hereby incorporated by reference for all purposes.

BACKGROUND

A method and apparatus for performing melting curve analyses of nucleic acids on a microarray is described herein.

Microarray technology evolved in the late 1980s and early 1990s from nucleic acid hybridization assays such as the Southern Blot and Northern Blot. The microarray technique is essentially a high throughput competitive hybridization with many different nucleic acid sequences of probes attached to an array surface, and many different sequences of target DNA. This technique has been adapted to a variety of applications, but some of the most common are gene expression profiling and single nucleotide polymorphism (SNP) analysis. In gene expression assays, mRNA is extracted from cells, converted to cDNA and simultaneously stained with fluorescent dyes before being hybridized to array chips containing complementary probes. The chips are allowed to dry, scanned via an array reader, and gene expression differences are calculated via software. In this procedure, the greater the level of gene expression, the more the fluorescent target DNA binds to the probes, and the stronger is the fluorescent signal. In SNP analysis, cDNA synthesis is omitted because genomic DNA is extracted from cells, is restriction digested, and then hybridized to chips (solid supports). In SNP analysis the array contains at least four probes for each SNP with a different base at the expected SNP, with a different base at the expected SNP site. The array reading process is the same for SNP analysis as for gene expression but some binding to all probes may be observed, and the correct SNP is measured by determining which probe has the most DNA binding.

Microarray techniques allow for high sample throughput. However, known microarray techniques exhibit reduction in accuracy and repeatability in comparison to high accuracy low throughput techniques. Like all other nucleic acid competitive binding assays, known microarray techniques suffer from the tendency of target DNA to bind the wrong probe, a condition known as promiscuous binding or mismatch. Promiscuous binding can be reduced by selecting the optimal hybridization temperature for a given sequence. However, because the array system may have several thousand different probe sequences on one array, it is practically impossible to optimize hybridization temperatures for all probes simultaneously. Rather an average hybridization temperature for all probes is calculated. But even under optimized conditions promiscuous binding still occurs. It is believed that this tendency, as well as lack of standardization in probe selection, is responsible for much of the error remaining in microarray analysis.

Although microarray techniques have produced valuable results, the standard application requires that results be validated using more accurate and expensive methods such as a real-time polymerase chain reaction (PCR). For gene expression experiments, the fold differences in expression of a single gene can vary as much as several fold between array results and real-time PCR validation results.

Methods for improving microarrays should deal directly with promiscuous binding issues. High accuracy, low throughput techniques such as real-time PCR, which is an enzyme-based test, are more accurate because of temperature-controlled hybridization of PCR primers. Therefore, double stranded product is only made if correct hybridization of primers to template takes place. During a typical real-time PCR experiment, it is possible to check the quality of the PCR reaction by examining the melting curve of the PCR product.

Melting curve analysis involves the use of heat to break the hydrogen bonds holding double stranded nucleic acids (most often DNA) together so that the double stranded form melts apart ("dissociates") into two single stranded products. The amount of heat required to melt DNA is dependent on the length, cytosine-guanine (C-G) content, and the complementarily of the double stranded form. In practice, special dyes such as SYBR Green I are among those used to monitor the exact temperature at which melting occurs. SYBR Green fluoresces 1000 times more when intercalated between double stranded DNA verses floating free in solution. As the temperature is raised, a large reduction in fluorescence indicates the melting of double stranded DNA and is usually depicted in a graph of fluorescence verses temperature. If mispriming takes place during real-time PCR reactions, the presence of a second PCR product with a different melting temperature would be evident, indicating that something went wrong with the reaction, and the experiment must be repeated under better conditions.

SUMMARY

The present disclosure relates to an apparatus and method for performing melting curve analyses of nucleic acids on a microarray. The present method includes providing a microarray having a plurality of probes covalently bonded thereto, wherein the microarray is covered with a coverslip, introducing a temperature controlled fluid into the sample chamber defined by the microarray and the coverslip, sequentially removing target DNA from the microarray by varying the temperature of the fluid at a temperature range corresponding to the melting temperature of the target DNA, scanning the mircoarray for fluorescence, collecting the target DNA removed from the microarray, and reusing the collected target DNA and the microarray.

Further noise reduction can be obtained by using advanced fluorescence analysis techniques Förster resonance energy transfer (FRET), fluorescence lifetime imaging (FLIM), and fluorescence correlation spectroscopy (FCS). In addition, raw data may be normalized by adjustment of the detector gain setting during repeated scans at different temperatures to adjust for photo bleaching effects.

The apparatus of the present disclosure includes a microarray stage, a light source and detector, and a temperature controller. The temperature controller is configured to adjust the temperature of a fluid within a sample chamber on the microarray so that the temperature of the fluid is varied during the analysis such that target DNA is dissociated from the microarray. The light source is directed to the microarray and resulting fluorescence is perceived by the detector.

One aspect of the present disclosure includes an apparatus for conducting a melting curve analysis of nucleic acids on a microarray by exciting a predefined portion of the microarray with a light beam and detecting emissions of fluorescent light. Such apparatus includes an illuminator assembly, including a light source configured to produce the light beam, the light beam comprising electromagnetic radiation having one or more wavelengths. The illuminator assembly may include a band pass filter configured to eliminate wavelengths close to the wavelength of fluorescent light emitted from the nucleic acids, a mirror configured to reflect the light beam and to allow the fluorescent light emission to pass through, and an objective lens configured to focus the light beam on a predefined portion of the microarray. The apparatus further includes an emissions detector configured to sense emissions of fluorescent light from the predefined portion of the microarray. The apparatus further includes a fluid circulation system, including a microarray cassette assembly including a frame including an opening configured to receive a microarray slide. The opening includes a spacer disposed about an inside perimeter. The fluid circulation system further includes a fluid inlet port, and a fluid outlet port, an optical window attached to the frame, and a seal disposed on the frame opposite the optical window. When a microarray slide is received within the opening, the spacer maintains the microarray slide separate from the optical window, the space between the microarray slide and the optical window defining a microarray chamber configured to allow the flow of fluid from the fluid inlet port to the fluid outlet port across the microarray slide. The fluid circulation system further includes a pump configured to receive fluid from a fluid reservoir and to circulate the fluid through a fluid supply line coupled to the fluid inlet port, a fluid return line coupled to the fluid outlet port. The apparatus further includes a temperature control assembly including a temperature controller, and a fluid heater. The apparatus of the present disclosure further allows the light beam and the microarray to be movable relative to each other.

Another aspect of the present disclosure includes a microarray cassette assembly for use in an apparatus for conducting a melting curve analysis of nucleic acids. The microarray cassette assembly of the present disclosure includes a frame, having an opening including an inside perimeter, the opening being configured to receive a microarray slide and a spacer disposed about an inside perimeter of the opening. The frame further includes an optical window attached to the frame and disposed on one side of the opening, a fluid inlet port, a fluid outlet port; and a seal attached to the frame opposite the optical window. The spacer is configured such that when the microarray slide is disposed within the opening, the microarray slide is spaced apart from the optical window, the space between the microarray slide and the optical window defining a chamber. Further, the chamber is configured to receive a fluid through the inlet port, the fluid having a flow that is distributed across the microarray slide, and discharged from the microarray chamber through the outlet port. The microarray cassette assembly of the present disclosure further includes a thermal block assembly for heating a microarray. The thermal block assembly includes a base configured to receive a microarray, a thermal block pivotally connected to the base, and configured to pivot between an open position and a closed position, and a heater coupled to the thermal block.

Another aspect of the present disclosure includes an apparatus for conducting a melting curve analysis of nucleic acids on a microarray by exciting a predefined portion of the microarray with a light beam and detecting emissions of fluorescent light. Such apparatus includes an illuminator assembly, having a light source configured to produce the light beam, wherein the light beam is composed of electromagnetic radiation having one or more wavelengths. The apparatus further includes an emissions detector configured to sense emissions of fluorescent light from the predefined portion of the microarray. The apparatus further includes a fluid circulation system, having a microarray cassette assembly defining a microarray chamber, the micro array cassette assembly including a fluid inlet port and a fluid outlet port. The fluid circulation system further including a pump configured to receive fluid from a fluid reservoir and to discharge the fluid through a fluid inlet line coupled to the fluid inlet port. The fluid circulation system further includes a fluid outlet line coupled to the fluid outlet port, and a temperature control assembly including a temperature controller configured to regulate the temperature of a fluid within the fluid circulation system. The apparatus further includes a microarray positioner, including a microarray cassette support movably attached to a base and configured to receive the microarray cassette, a first support positioner attached to the base and configured to directionally move the microarray cassette support along a first axis, and a second support positioner attached to the base and configured to directionally move the microarray cassette support along a second axis, the second axis being perpendicular to the first axis.

Another aspect of the present disclosure includes a method for performing a melting curve analysis of nucleic acids on a microarray slide by a microarray reader. The method comprising the steps of: initializing the microarray reader; initializing the microarray slide; acquiring data; processing the data; and analyzing the data. The initializing the microarray reader step further includes the steps of: focusing a scanner included in the microarray reader; performing a preview scan; and assigning a scan area. The acquiring data step further includes the steps of: heating the microarray slide to a predetermined temperature; allowing the microarray slide to dwell at the predetermined temperature for a predetermined period of time; flushing the microarray slide with a predetermined fluid volume; and scanning the microarray slide. The microarray slide may be heated by providing a continuous flow of heated fluid, and wherein the flow rate of the heated fluid is increased during flushing. Also, the temperature of the fluid may be increased during flushing to increase the temperature of the microarray. These steps may be repeated at multiple increasing temperatures. The processing data step further includes the steps of: opening a first scanned data file; opening a generic feature list file; geographically aligning the generic feature list to the first scanned data file; defining unique feature shapes for each microarray spot on the microarray slide; and storing the custom feature list data. The analyzing data step further includes the steps of: opening a custom feature list file; creating a composite results file; opening a scanned image file; geographically aligning the custom features list to a scanned image; measuring the intensity of each feature; creating a file to store feature data; normalizing feature intensity values; and storing the composite results. The normalizing feature intensity values step includes the further steps of setting an initial geographic alignment of custom features for each probe spot on a microarray slide; and comparing the intensity of each feature based on the initial geographic alignment.

BRIEF DESCRIPTION OF THE DRAWINGS

The present disclosure will be described hereafter with reference to the attached drawings which are given as non-limiting examples only, in which.

DETAILED DESCRIPTION

Figure 1:
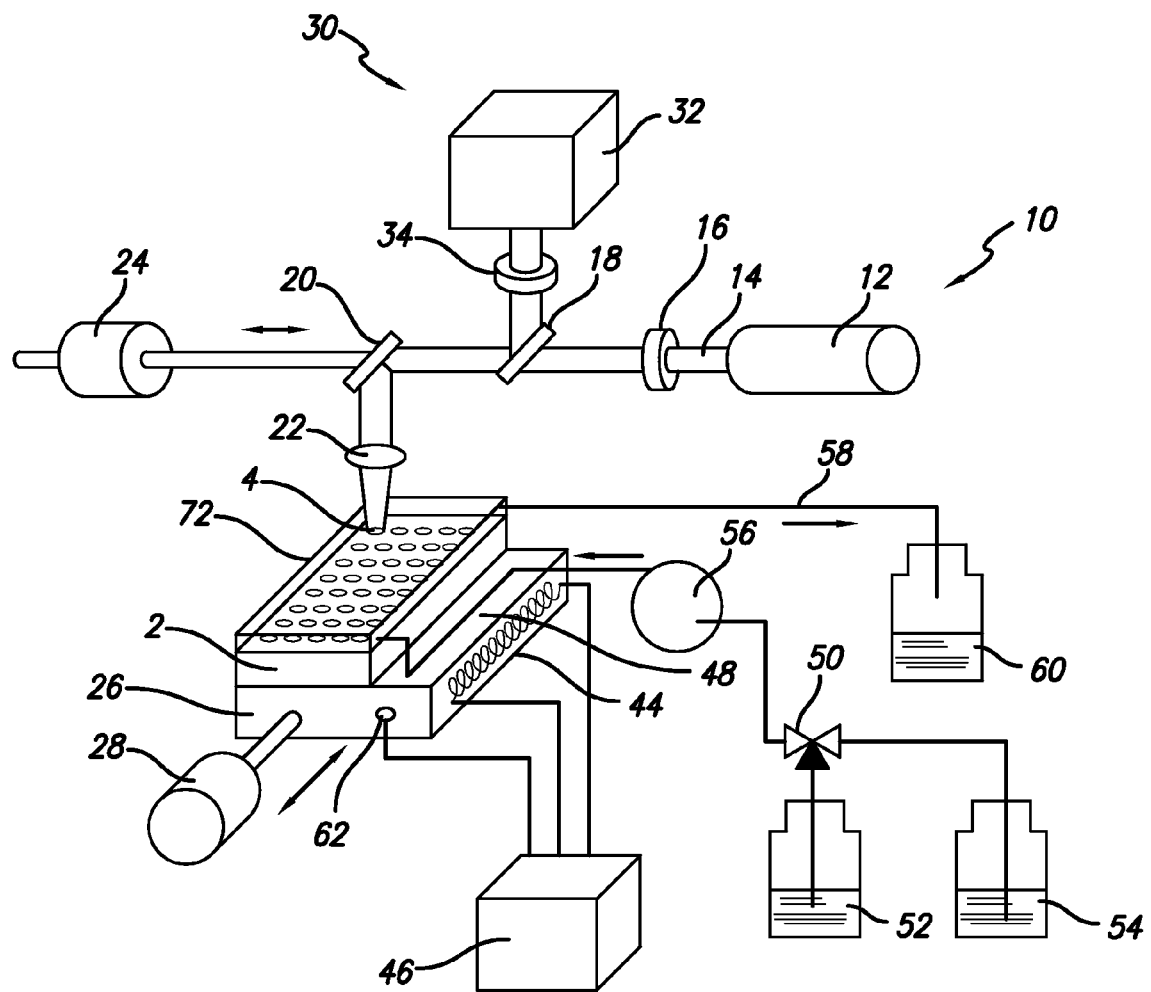
FIG. 1 is a schematic representation of an exemplary embodiment of the microarray analysis apparatus and system of the present disclosure in which a thermal block is used to pre-heat circulating fluid and to control the temperature of the microarray.

While the present disclosure will be described fully hereinafter with reference to the accompanying drawings in which particular embodiments are shown, it is understood at the outset that persons skilled in the art may modify the disclosure herein described while still achieving the desired result of this disclosure. Accordingly, the description which follows is to be understood as a broad informative disclosure directed to persons skilled in the appropriate arts and not as limitations of the present disclosure.

While it is not possible to completely prevent promiscuous binding on the microarray, using a melting curve to double check the results can be applied so that the presence of mis-binding can be detected and quantified. In this approach each gene or expressed sequence tag (EST) has a probe that is designed using various software applications to melt at a predetermined temperature (for example 65° C.).

In the apparatus and system of the present disclosure, each probe is attached to a microarray slide or chip 2 at its individual array probe spot 4 and hybridization is performed in a manner similar to a conventional microarray but inside a custom hybridization and melting chamber at a controlled temperature with a moderate level of stringency. During hybridization under conditions of moderate stringency, binding is favored for perfectly matched target and SNPs but not to target with multiple mismatches. Hybridization may be performed inside the reading instrument or outside in a hybridization oven. Instead of drying the chip, buffer fluid is left on the array, a series of washings are done using a fluid flush of buffer through the chamber removing un-hybridized target DNA. Then the chamber is oriented in the reading instrument with the cover slip window facing the optical system. The temperature is ramped upward in increments which may range from 5° C. to 0.01° C. The time allotted to each temperature change may range from 1 minute to several hours.

Each probe spot 4 on the microarray 2 is scanned for fluorescence with loss of fluorescence indicating that double stranded DNA is melting into single stranded DNA. This is measured in a predetermined fluorescence acquisition window (for example 55°-75° C.). If junk or background DNA with a low affinity are attached to a given probe, the junk or background DNA would melt before 55° C. and would not be included in the measurement. If probes attached to target DNA which contained a perfect complementary sequence melting will occur at approximately 65° C. One base pair mismatches which are SNPs would also melt in the fluorescence acquisition window (55°-75° C.) but these melting curves would be separate from the perfect match curves by being several degrees lower. The relative concentration of each product (perfect match vs. SNP) is measured by measuring the area under each curve or peak. Therefore, background is eliminated, the relative amount of mismatch vs. perfect match quantified, and the presence of SNPs confirmed.

Melting point analysis improves the signal to noise ratio by reducing the noise caused by misbound target DNA leading to more accuracy. Further improvements in the signal to noise ration can be obtained by using advanced fluorescence spectroscopy techniques such as FRET, FLIM, or FCS. Each of these techniques has the ability to distinguish target DNA which is bound to probe DNA from target DNA which is nearby but not bound to probe DNA. Also, these techniques can be used together or separate from each other.

FRET uses two fluorescent dyes known as FRET partners and can be used to indicate that two complementary strands of DNA are within or less than 10 nm of each other. The donor FRET partner is attached to one strand of DNA can become excited and transfer its energy to the acceptor dye present on the other complimentary DNA strand. Therefore, exciting the donor dye results in emissions from the acceptor dye. However, the acceptor strand must generally be within 10-15 nm or less in distance for this effect to occur. The detection of FRET is an indication that complementary strands of DNA are likely bound to each other and not melted apart.

FLIM measures the decay rate of the excited state (the "fluorescence lifetime") rather than fluorescence intensity. Since the micro environment in which a fluorescent dye is present can affect the decay rate, FLIM can be used to determine if a DNA strand is single stranded or double stranded based on differences in fluorescence lifetime.

FCS uses an autocorrelation function to measure the diffusion rate of fluorescent particles. This function can be used to determine if a fluorescently labeled DNA strand is bound to another verses unbound.

Detecting and quantifying the amount of perfectly matched target DNA to probe, and the amount of mismatched binding has three advantages:

First, there is improvement in accuracy of gene expression profiling. During a standard microarray there is no method to determine the quantity of bound DNA which is correct target DNA with a perfect match, to probes, versus mismatched DNA with one or two base pair mismatches. Melting curve analysis allows precise measurement of the amount of perfectly matched DNA bound, thus, improving the overall accuracy of the test and eliminating the need for validation assays.

Second, the ability to confirm a one base pair mismatch between probe and target DNA serves as confirmation of the presence of SNPs. Standard arrays commonly use a series of 4 probes or more with different bases at the SNP site. Then the array reader determines which probe has more target bound. Even with multiple probes involved, there is no way to confirm the results, and this technique is especially error prone when probe sequences have repetitive sequence elements. Melting curve analysis precisely measures the amount of mismatch to perfect match for each probe, and eliminates the need for validation assays.

Third, is the ability to reuse both the array and sample. At the end of an assay, the sample is melted off the array, collected for reuse, and both the array and sample are stored for further experimentation. Improvements in probe binding technology by using covalent bonds have made some microarrays reusable up to five times. Dilution problems caused by the dynamic range of gene expression in a cell are also eliminated by array reuse. Different genes can be expressed under a wide range of levels. If expression is too high, array probes will be saturated. If expression is too low, no binding will occur. Since it impossible to predict gene expression levels before doing a gene expression assay, the experiment often needs to be repeated several times at different dilutions. By using a real-time array procedure, the sample can be melted off the array, the dilution adjusted, then the same chip and sample reused for serial dilutions, eliminating the need for multiple chips.

The real-time array process of the present disclosure is a microarray technique for use with conventional microarray chips. For example, standard size 25 mm×75 mm slide microarrays with probes already bound via a covalent bonding procedure can be used from a variety of manufacturers. A glass or silicone heat resistant hybridization-melting cover slip with a silicone gasket is attached to the surface. A small volume (10-400 μl) of sample is introduced into the chamber and the chamber sealed. A nucleic acid sample is allowed to hybridize to the chip, but the buffer is left on the array after hybridization with a cover slip over the buffer. This is in contrast to the processing of a standard microarray chip in which the cover slip is removed, the array rinsed, and allowed to dry before reading takes place. The chip is placed in the reader machine and the fluorescence intensity is measured repeatedly for each probe spot on the array as the temperature of the chip is progressively increased. For each probe, a melting curve is generated by combining the fluorescence intensity data at each temperature reading.

Software analysis of the data curve determines the presence of one base pair mismatches which are SNPs and the presence of greater than one base pair mismatches which are noise. Junk nucleic acids or noise bound to probes will melt at a much lower temperature than perfectly matched target bound to probes and this source of error is eliminated from the measurement. SNPs which contain a one base pair mismatch will melt at a slightly lower temperature than perfectly matched target DNA and can be easily distinguished and accurately measured. Therefore, the presence of SNPs is validated and noise eliminated from any procedure (e.g. gene expression profiling, SNP analysis, and so forth).

This process can be performed in two formats. The first is a fluidics method which involves pumping buffer across the array. The second is a stationary buffer method which involves no buffer flow through. Each method requires a corresponding apparatus as described herein.

Fluidics Method and Apparatus
 a. Apparatus Description

The real-time array fluidics system of the present disclosure includes of five subsystems depicted in FIG. 1. These subsystems are: an illumination system 10, an emissions detection system, a fluid circulation system, a microarray translation stage, and the thermal control subsystem.

The illumination system 10 used to image the microarray 2 includes a light source 12 such as a laser, arc lamp, LED, or other suitable form of illumination. The illumination system 10 is currently shown as confocal illumination but other approaches could be used. The light source 12 produces a light beam 14, which passes through an excitation filter 16.

The excitation filter 16 is used to eliminate light in the wavelength range close to the emissions of the fluorophore. The excitation filter 16 may be constructed as a bandpass and/or dichroic type filter. After the light beam 14 passes through the excitation filter 16, the light beam passes through a beam splitter 18 configured to pass the light beam 14 but not the fluorescence emission wavelength. The beam splitter 18 can be constructed of dichroic filter material. The light beam 14 is then reflected by a scanning mirror 20 and focused onto the microarray 2 using an objective and/or a focusing lens 22. In the embodiment shown in FIG. 1, the scanning mirror 20 is connected to a translation actuator 24 configured to move the scanning mirror relative to the microarray 2 in an "X" direction. The light beam 14 is focused to excite the spots 4 on the microarray 2.

The embodiment of FIG. 1 further includes a stage 26 to support the microarray 2. The stage 26 is connected to a translation actuator 28 configured to move the microarray relative to the scanning mirror 20 in an "Y" direction, which is substantially perpendicular to the "X" direction of the scanning mirror 20. The array motion system provides a 2-directional motion using the stage 26. The "Y" translation actuator 28 is used to move the microarray 2 in one direction and "X" translation actuator 24 is used to translate the scanning mirror 20 and objective lens 22 across the microarray 2 in a direction 90 degrees to the "Y" motion. This motion allows the system to scan the entire area of the microarray 2 looking for spots 4 fluorescence. Other types of motion devices could be used like; linear motors, rack and pinion gears, or other similar means.

The fluorescence detection system 30 is based on a high sensitivity sensor 32, for example a photomultiplier tube, avalanche photodiode and/or another type of photo sensor. A digital camera may also be used as sensor 32. Fluorescent light emissions from the microarray 2 are collected by the objective lens 22. The collected light follows the path of the light beam 14 to the mirror 20 and is reflected to the beam splitter 18. The beam splitter 18 has a selective coating that allows the light emissions from a fluorescing microarray spot 4 to be reflected towards the sensor 32 rather than being redirected towards the light source 12. The emitted light then passes through a dichroic emissions filter 32. However this filter may not be required if a laser, LED, or other monochromatic light source is used because of the precision of the wavelengths emitted. The fluorescent emissions then are directed into the sensor 32. Depending on the sensitivity of the system many different sensors could be used to measure the level of fluorescence emissions, as discussed previously.

Figure 2:
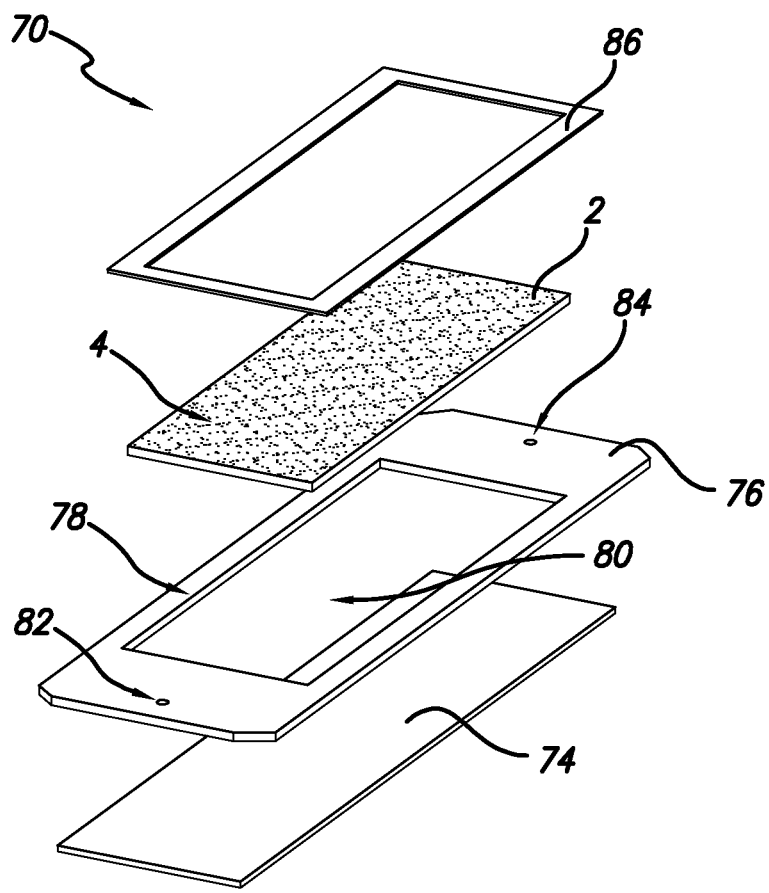
FIG. 2 is a schematic representation of a microarray chamber used deliver circulating fluid to the microarray and to control the temperature of the microarray.
Figure 3:
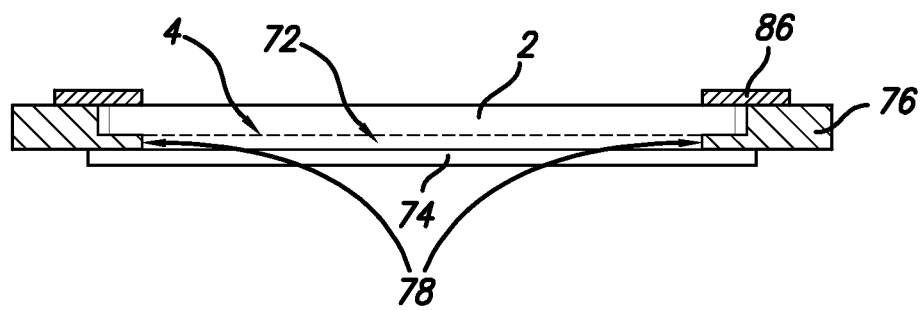
FIG. 3 shows a cross section of the microarray slide and chamber shown in FIG. 2.
Figure 4:
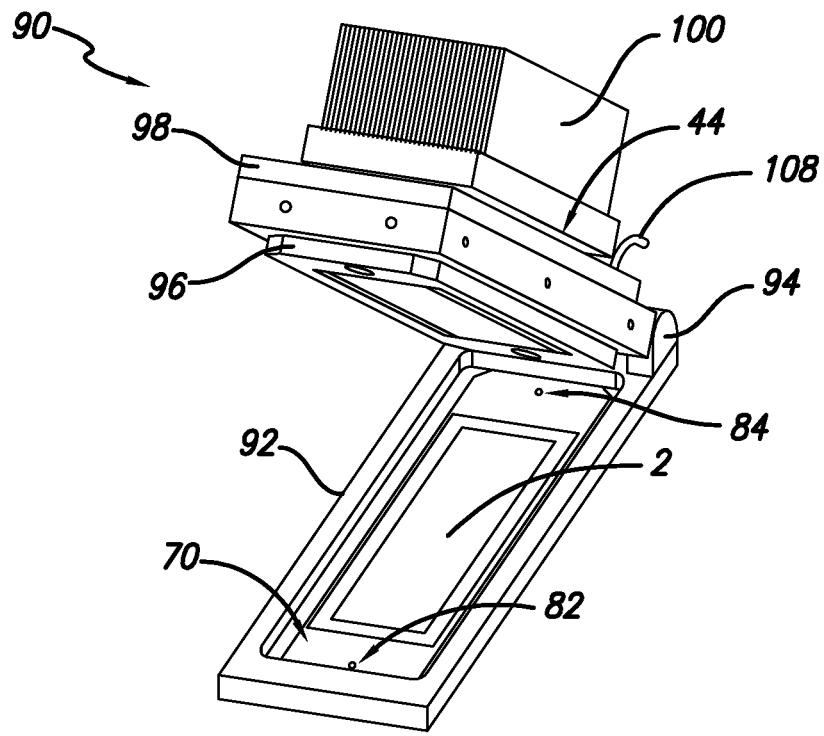
FIG. 4 is a perspective view of an exemplary embodiment of the thermal control and buffer delivery sub-systems, with the microarray chamber in an open configuration.

A microarray chamber 72, is defined by the space between the microarray 2 and an optical window 74, or cover slip, as shown in FIGS. 2 and 3. Microarray chamber 72 holds and/or delivers fluids to the microarray 2. The microarray chamber 72 is in intimate contact with a heater block 96, as shown in FIG. 4. The heater block temperature is accurately controlled by a heater 44 and the heater controller 46. Solutions are introduced to the chamber through a preheater 48 within the heater block 96. The preheater 48 is designed to equilibrate the temperature of the incoming fluids to the temperature of the microarray chamber 72 and the microarray 2.

The solutions introduced into the microarray chamber may be a hybridization solution, a buffer solution, or other fluid. Selector valve 50 can be used to select a solution from one or more fluid reservoirs 52, 54, such as hybridization solution (reservoir 52) or a buffer solution (reservoir 54) as shown in FIG. 1. To introduce hybridization solution from reservoir 52 into the microarray chamber 72, selector valve 50 is opened to hybridization solution reservoir 22 and a pump 56 is turned on long enough to fill the microarray chamber 72. The temperature of the heater block 96 is controlled to the appropriate temperature for good hybridization. The hybridization step can be done prior to loading the microarray 2 onto the apparatus.

After hybridization is complete and the apparatus is ready, the temperature of the heater block 96 can be changed to the starting temperature. After the starting temperature is reached the selector valve 50 selects the buffer solution from reservoir 54 and the pump 56 is used to push the hybridization solution out of the microarray chamber 72.

After the temperature is stabilized the fluorescence scanning system scans the microarray spots 4 and the fluorescence levels are recorded. The fluid in the microarray chamber 72 is then flushed to remove unbound fluorescent tags from the microarray chamber 72. The waste solutions travel through the waste line 10 to the waste reservoir 60.

After this initial read is complete, temperature ramping process is started. The temperature of the microarray 2 is increased by one step changing the input to the temperature controller 46. Again, after the temperature is stabilized, a fluorescence scan of the microarray 2 is completed, the intensities of the fluorescence is recorded. This temperature change, read step, and flush process is repeated for the temperature range of interest. The temperature controller 46 further may include a temperature sensor 62 to give feedback to the controller 46 to accurately control the temperature of the heater block 96. The heater 44 may be a resistive heater and/or any other type of heater such as a Peltier thermal electric element.

b. Microarray Chamber Description

Referring to FIGS. 2 and 3, the microarray chamber 72 is shown in the inverted orientation from the system description and the spots 4 are on the bottom surface of the microarray 2. The microarray 2 is retained by a cassette 70 including a frame 76. The frame 76 positions the microarray 2 with respect to the optical system and to space it off the optical window 74. The frame 76 includes a spacer 78 at disposed about an opening 80 in the frame 76. Micro array chamber 72 allows fluid flow between the microarray 2 and the optical window 74.

Fluids are introduced into the microarray chamber 72 at an inlet port 82 and flow transversly across the microarray 2 to the outlet port 84. The optical window 74 is sealed to the frame 76. The microarray 2 is held in place by a seal 86. Other means of sealing the microarray 2 in the frame 76 may also be used, such as an adhesive or a thermal seal. This cassette assembly 70 loads into a thermal block assembly 90 as described below.

c. Thermal Block Assembly Description

Figure 5:
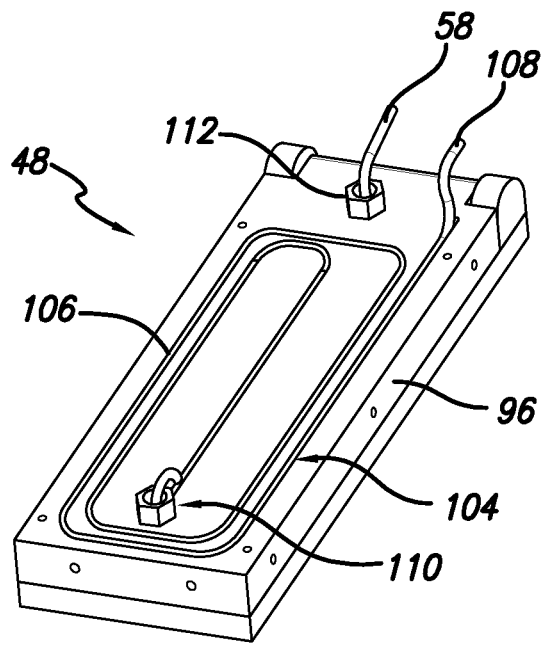
FIG. 5 is a top perspective view of a microarray chamber in a closed configuration showing the circulating fluid pre-heater sub-system.

The thermal block assembly 90 is a means of connecting the cassette assembly 70 to the fluid flow system and the thermal controller. Referring to FIGS. 4 and 5, the thermal block assembly 90 is supported by a base frame 92. The frame is attached to the translation stage 26. The base frame 92 is used to support the microarray cassette assembly 70. A hinge 94 connects to the heater block 96 to the base frame 92. The hinge 94 allows the heater block 96 to pivot allowing access to the microarray cassette assembly 70. In the embodiment shown in FIG. 4, a Peltier device is used as the heater 44 to provide heat energy for the heater block 96. Other type of heaters may also be used, such as a resistive heater or a circulating fluid. A heat plate 98 is used to transfer the heat generated by the heater 44 to the microarray 2 through the heater block 96. Attached to the Peltier heater 44 shown in FIG. 4 is a heat sink 100 for adding or dissipating heat that is generated by the Peltier heater 44. The heater block 96 includes a contact surface 102 that makes direct contact with the microarray 2. This direct contact helps keep the temperature of the microarray 2 at a uniform temperature.

FIG. 5 shows the thermal block assembly 90 with the heater 44 and heat sink 100 removed to reveal the fluid preheater 48. Preheater 48 includes tubing 104 disposed within a channel 106 within the thermal block 96. Tubing 104 includes a preheater inlet 108 through which the fluid is introduced. The temperature of the fluid is brought to the temperature of the thermal block 96 by conduction through the tubing 104. At the end of the tubing 104 the fluid is introduced to the microarray chamber 72 through an inlet coupling 110 which corresponds to inlet port 82. Waste fluid exits the microarray chamber through the outlet port 84 corresponding to outlet coupling 112 and then flows through a waste line 58.

d. Fluidic Preheater Apparatus Method

The real-time array fluidics method is performed with any of the common dyes used for either one color of two color microarray assays (e.g. Cy3 or Cy5). In conventional arrays, the target DNA has been permanently stained and will fluoresce when bound to probes and when floating in solution. The presence of non-bound fluorescent DNA will produce unwanted background and thus noise in the system. This problem is eliminated by using a small and even flow of buffer pumped across the microarray slide 2 but under the optical window 74 so that melted target DNA can be removed from the array during temperature ramping.

There are a variety of formats for performing this procedure. The first is a simple cycle of temperature increase, followed by a pulse of buffer to flush through the chamber to remove melted target DNA through the heated buffer waste line 58 which is deposited in a waste collection reservoir 60. Then the microarray 2 is scanned to measure the remaining fluorescence using the X and Y translation actuators 24, 28.

Another embodiment uses a continuous flow of temperature controlled buffer through the microarray chamber 72 which helps to keep the temperature as constant as possible by compensating for losses of heat. Then alternating cycles of temperature increase followed by scanning are performed to measure the remaining fluorescence on the microarray 2.

Yet another embodiment is a variable cycle consisting of temperature increase followed by microarray scanning in which the buffer flush is omitted for several cycles of temperature increase and scanning to save time and buffer. For example, after at least two cycles or more of temperature increase and scanning have taken place the array is flushed with buffer. Then the cycle of temperature increase and scanning are repeated at least twice followed by one cycle of buffer flush.

For each embodiment, the temperature increases which removes the melted DNA to the waste collection reservoir 60 and scanning of the microarray 2 via the objective lens 22 is repeated in cycles until all the DNA has melted off the microarray chip 2. For each probe spot 4, a graph of fluorescence intensity verses temperature is then plotted using software.

This method has the ability to detect mismatched target DNA and SNPs by determining the exact melting temperature, will work with any array system using covalent bonding to attach target DNA to glass slide, and with any dye color system commercially available. Furthermore, since the released target DNA is collected in a waste reservoir 60, the sample can be purified and reused for another experiment.

The option to reuse target DNA is useful, especially for difficult to obtain samples.

Stationary Buffer Method

An alternative approach to providing temperature control is the use of a resistance heater 44 which is used to directly heat or cool the microarray 2 rather than the circulating fluids.

The illumination, detection and motion system are similar to those of the buffer thermal control system described herein. The microarray 2 is mounted on top of heater block that includes a temperature sensor 62 and a heating and/or cooling element 44. The temperature sensor 62 produces a signal that is fed into the temperature controller 46. This controller 46 sends a signal to the heating/cooling element 44 to accurately control the temperature of the microarray 2. The temperature of the microarray 2 can be changed incrementally or ramped.

Figure 6A:
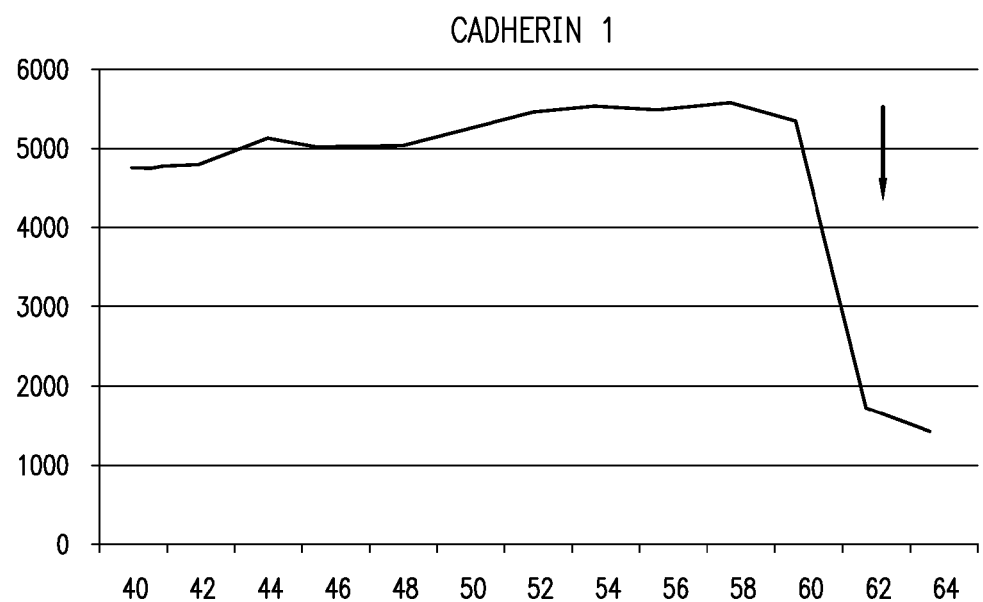
FIGS. 6A and 6B are plots of relative fluorescence values obtained through melting curve analysis for two probe spots on a microarray.
Figure 6B:
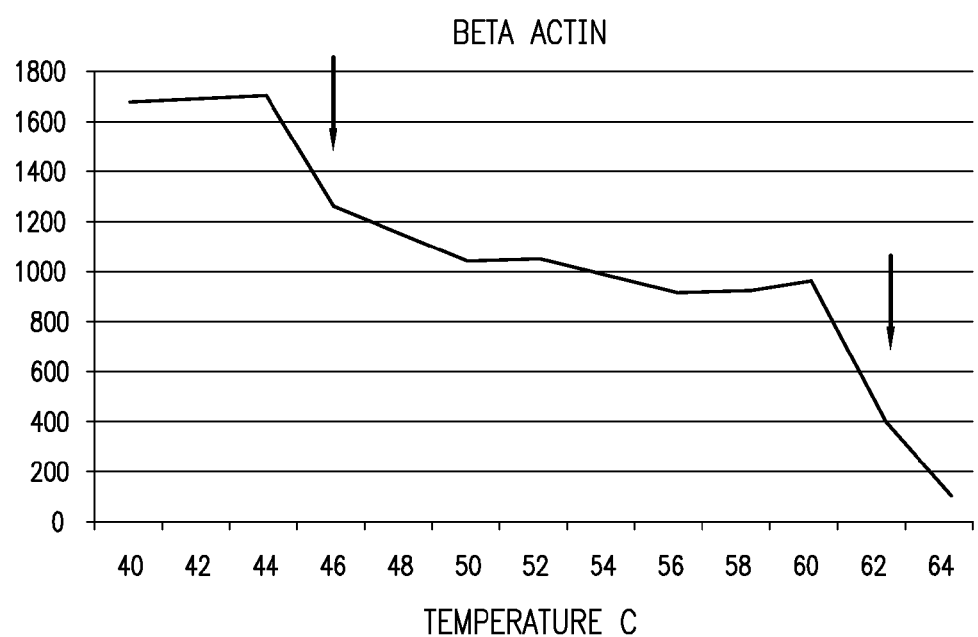

After hybridization is complete, the microarray 2 is progressively warmed via the heating element 44 positioned below the array 2 and the melting of target DNA bound to probe DNA is monitored using special fluorescent dyes. There are two distinct types of dyes that are suitable for this application. An intercalating dye such as SYBR Green I, or a minor grove binding dye such BEBO. These dyes fluoresce only when DNA is double stranded. As the temperature is ramped upward, loss of fluorescence indicates that double stranded DNA is melting into single stranded DNA, and can be measured in a predetermined temperature window. For each probe spot 4, a graph of fluorescence intensity verses temperature is plotted with software as shown in FIGS. 6A and 6B.

Alternatively, any of the standard dyes used for microarray can be used in combination with an advanced fluorescence techniques such as FRET, FLIM, or FCS. These techniques are capable of distinguishing target DNA bound to probe or nearby but not bound to probe DNA eliminating any background signal caused by melted target DNA which is in the vicinity or the probe spot.

Probe Spot Analysis

After each temperature scan has taken place, a digital image file is generated for fluorescence intensity analysis. For each probe spot on the image, software traces the edge of the probe spot to set a boundary between the spot and other areas of the microarray. The probe spot is generally circular in shape but may also be square or irregular in shape. Once the probe spot boundary is determined, the mean or median fluorescence intensity is calculated for the pixels within the boundary. The exact location, shape, and area of the probe spot boundary is recorded and replicated as new image files are created at higher temperatures for fluorescence intensity analysis. Consistency of probe spot analysis throughout the experiment is essential for accurate melting curve determination. In addition to just tracing the edge of the probe spot of the first image obtained, a fix shape such as circle or other geometric shape with fixed diameter may also be used. Again, the exact location, shape, and area of the shape used to define the boundary of the probe spot must be replicated for each subsequent image to insure constancy of fluorescence analysis and melting curve determination. A flow chart outlining the operation of the apparatus of the present disclosure is shown in FIGS. 10A-10D.

Melting Curve Data Analysis Method

As shown in FIGS. 6A and 6B, analyses performed using commercially available microarrays obtained from Arrayit Corp. of Sunnyvale, California and human cDNA target stained with Cy3 dye obtained melting curves for probe spots initially having sufficient fluorescence. Of these the melting curves have been plotted for two particular probe spots, comparing the two spots on the same array. FIG. 6A shows a graph of a probe spot for Cadherin 1 yielded a curve with only one major melting point with a $T_m$ of about 63° C. indicating only one major hybridization product. However, FIG. 6B is a graph of the Beta Actin probe spot yielded a melting curve with at least two major melting points with a $T_m$s of about 46° and 62° C. This indicates that at least two hybridization products were formed and the product melting at the lower temperature would contain mismatch in its target sequence. Also, the relative concentrations of each hybridization product can be inferred from the graph. If the sequence of the probes is known, the melting temperature can be estimated to determine if binding is nonspecific noise or the presence of an SNP. Conventional microarray technology cannot obtain this type of information.

The melting temperature is unique to the specific DNA under analysis. After the melting temperature is reached the rate of change of intensity is reduced back to a value similar to the pre-melting temperature. The slope of the graph can also be used to show the melting temperature. The slope of the melting curve is another method to identify the melting point. The slope or rate of change of the intensity for a given temperature step give a clear indication of the melting point.

Fluorescence Correlations Spectroscopy (FCS) Alternative Detection Modality

Figure 7:
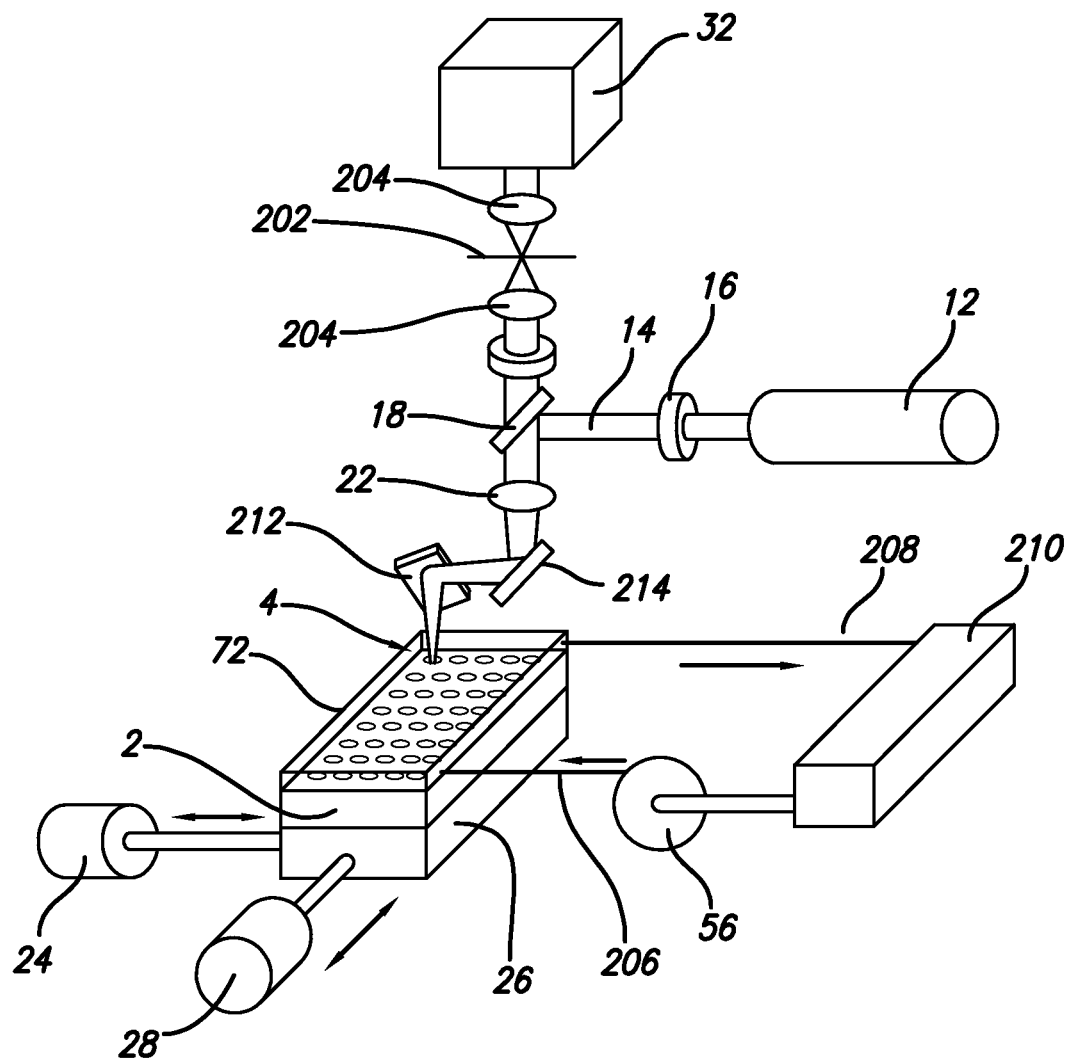
FIG. 7 a schematic representation of another embodiment of the present disclosure depicting a real time array apparatus and system including fluorescence correlation spectroscopy to increase detection sensitivity.
Figure 8:
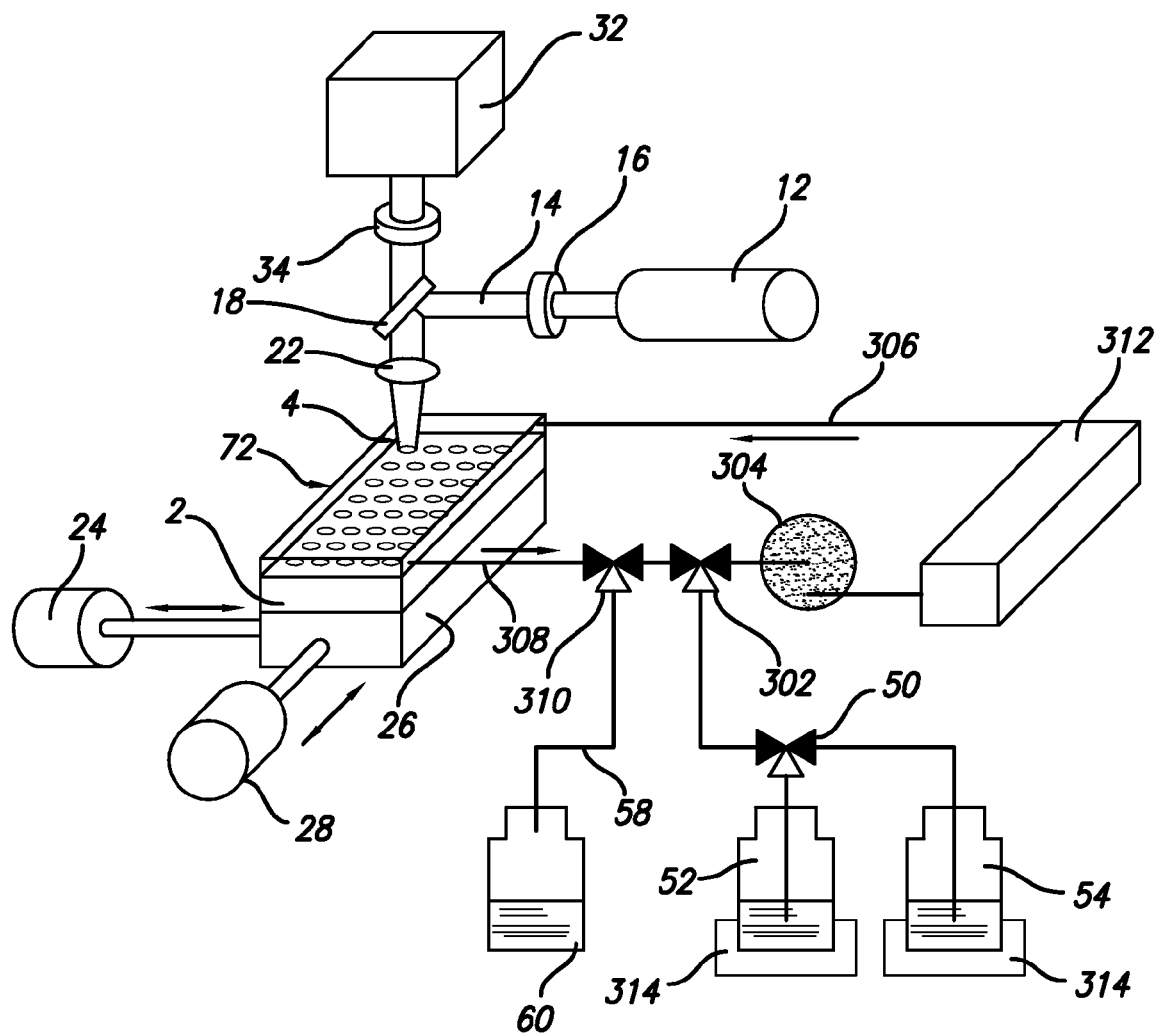
FIG. 8 a schematic representation of another embodiment of the present disclosure depicting a real time array apparatus and system with circulating buffer.

Fluorescence correlation spectroscopy (FCS) as depicted in FIG. 7 may be used as an alternative method of fluorescence analysis. Traditional methods of studying the melting of double stranded nucleic acids using fluorescence, measure the separation as a function of the reduction of fluorescence. In contrast FCS, can measure the separation of double stranded nucleic acids as a change in the diffusion. This type of analysis is compatible with the apparatus shown schematically in FIG. 1, configured with a pin hole 202 and an additional lens 204. This type of analysis id also compatible with a standard confocal laser-scanning microscope configured with a pinhole 202 and additional lens 204, and is also compatible with a two-photon laser scanning microscope.

With relation to the buffer thermal control method and apparatus, FCS imagining analysis takes place in the same fashion as previously described. After hybridization, the microarray chip 2 is placed on translation stage 26. The temperature controlled buffer supply line 206 and heated buffer return line 208 are connected to a heater 210. As the temperature is raised, a pulse of heated buffer which enters the microarray 2 via the temperature controlled buffer supply line 206 removes melted target DNA through heat buffer return line 208 which is deposited in a waste collection reservoir through a three-way valve (not shown in FIG. 7). Then the microarray 2 is scanned to measure the remaining fluorescence using the X and Y translation motors 24, 28 to move the translation stage 26 and microarray 2 move back forth while the objective lens 22 scans and collects the emitted light which is transmitted through the optics and its intensity is measured by the sensor 32. Scanning mirrors 210, 212 may also be used in conjunction with translation motors 24, 28 to scan microarray spots 4.

The only specific requirements for FCS are that the optical system must have a pin hole 202, as shown in FIG. 7 with additional lenses 204 and that the computer software processes the fluorescence data using a correlation function contained in a computer processing chip or card. There are several advantages to incorporating FCS. This analysis procedure is more sensitive and can accurately detect one molecule of target DNA. It has the ability to simultaneously distinguish between target DNA bound to probe and target free in solution by measuring and comparing the diffusion rates. Also it is not reliant on fluorescence intensity to determine if DNA has melted apart and diffusion rate can also yield some information about the molecular weight of the target DNA.

Circulating Buffer Apparatus

The circulating buffer apparatus is a variation of the Fluidic Preheater Apparatus discussed previously. In this embodiment, the circulating fluid is used to control the temperature of the microarray 2. The excitation, emission, and scanning or translation sub-systems for the Circulating Buffer Apparatus are the same as the Fluidic Pre-heater Apparatus, only the temperature control sub-system is different.

A microarray chamber 72 holds and/or delivers reagents to the microarray. The reagents and/or buffer have two purposes. The first is to keep the microarray 2 wet and the second is to control the temperature. The circulating system has a reagent/buffer supply valve 302 that is used to introduce new reagents to the microarray and or to circulate existing reagents/buffers. If the reagent/buffer supply valve 302 is in the circulation mode, pump 304 is used to circulate the fluid through; a supply line 306, the microarray chamber 72, a return line 308, a waste three-way waste valve 310, a heat exchanger 312 or temperature controller, and back through the reagent/buffer 3-way supply valve 302.

To introduce new reagents or buffers to the system both three-way valves 302 and 314 can be switched to allow reagents/buffer to be introduced from reservoirs 52, 54. Excess reagent/buffer in the loop is directed to the waste line 58 and to the waste reservoir 60. A selector valve 50 may be used to deliver multiple reagent types to the microarray 2. Although two bottles are shown, a plurality of bottles may be used.

The thermal control system includes a temperature controller or heat exchanger 312. This heat exchanger is used to set the temperature of the reagent/buffer circulating through the microarray 2. The heat exchanger 312 holds the temperature of the fluid fixed while a fluorescence scan of the microarray 2 is completed. The heat exchanger 312 is also used to change the temperature of the reagent/buffer to acquire melting curves for the microarray 2.

For rapid changes in array temperature a bottle pre-heater 314 may be used. The bottle pre-heater temperature is set such that the temperature of the reagent corresponds to the next desired temperature. After the microarray scan is completed; a new infusion of reagent at the different temperature is introduced. The infusion of the new temperature may be configured to create rapid temperature changes above 1 degree C. per second. This rapid reagent temperature change reduces the overall read times of the microarray 12.

Fluorescence Intensity Normalization Method

Figure 9:
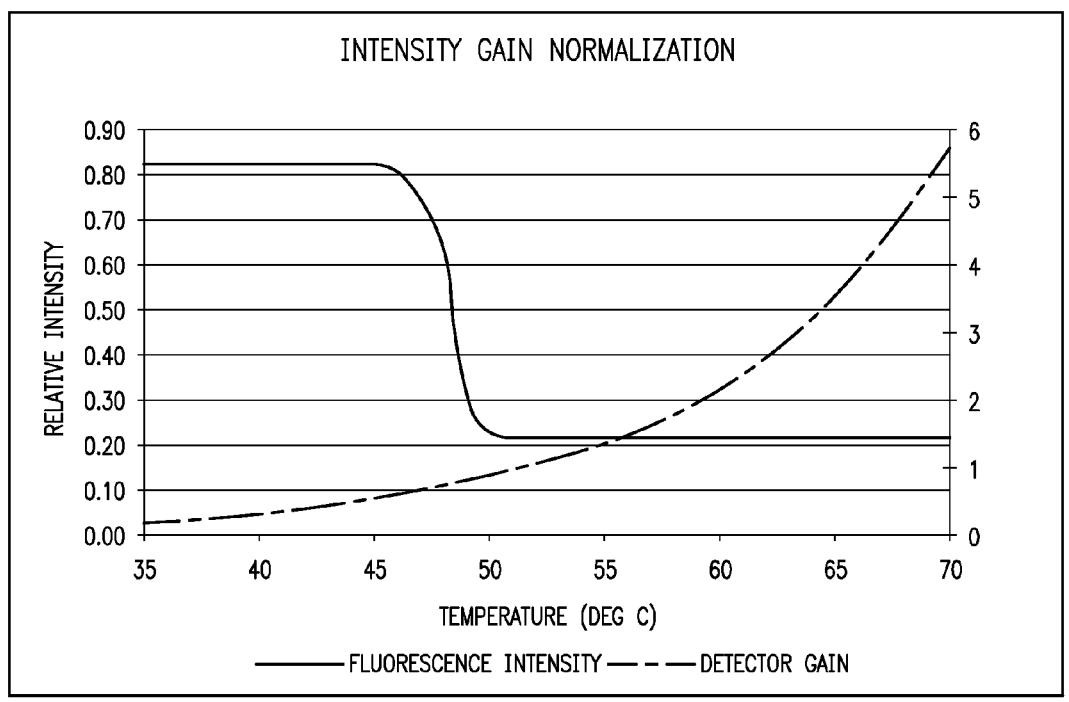
FIG. 9 is an example of a melting curve with gain fluorescence intensity normalization.
Figure 10A:
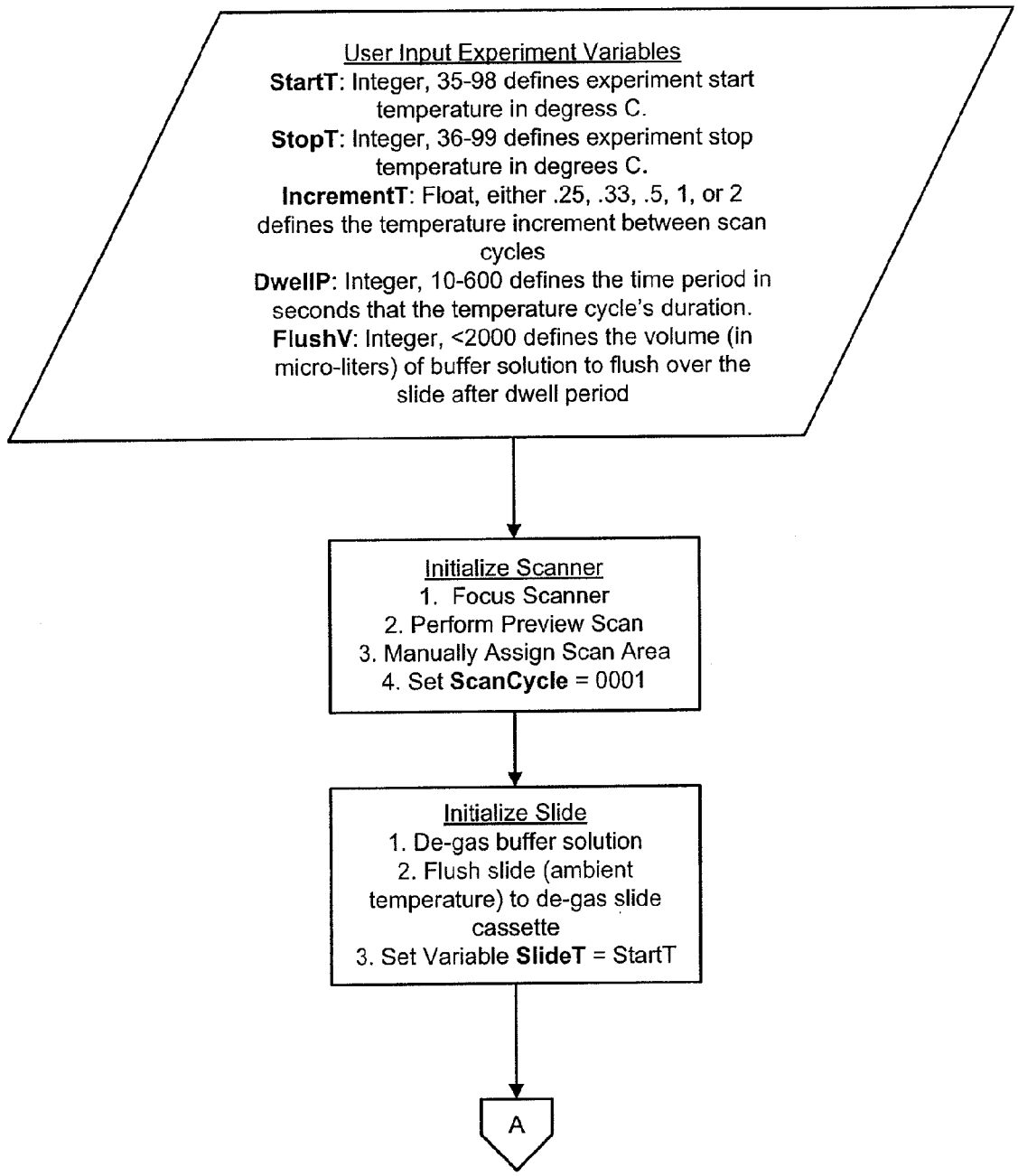
FIGS. 10A-10D are a flow chart showing the operational steps of the apparatus and system of the present disclosure.
Figure 10B:
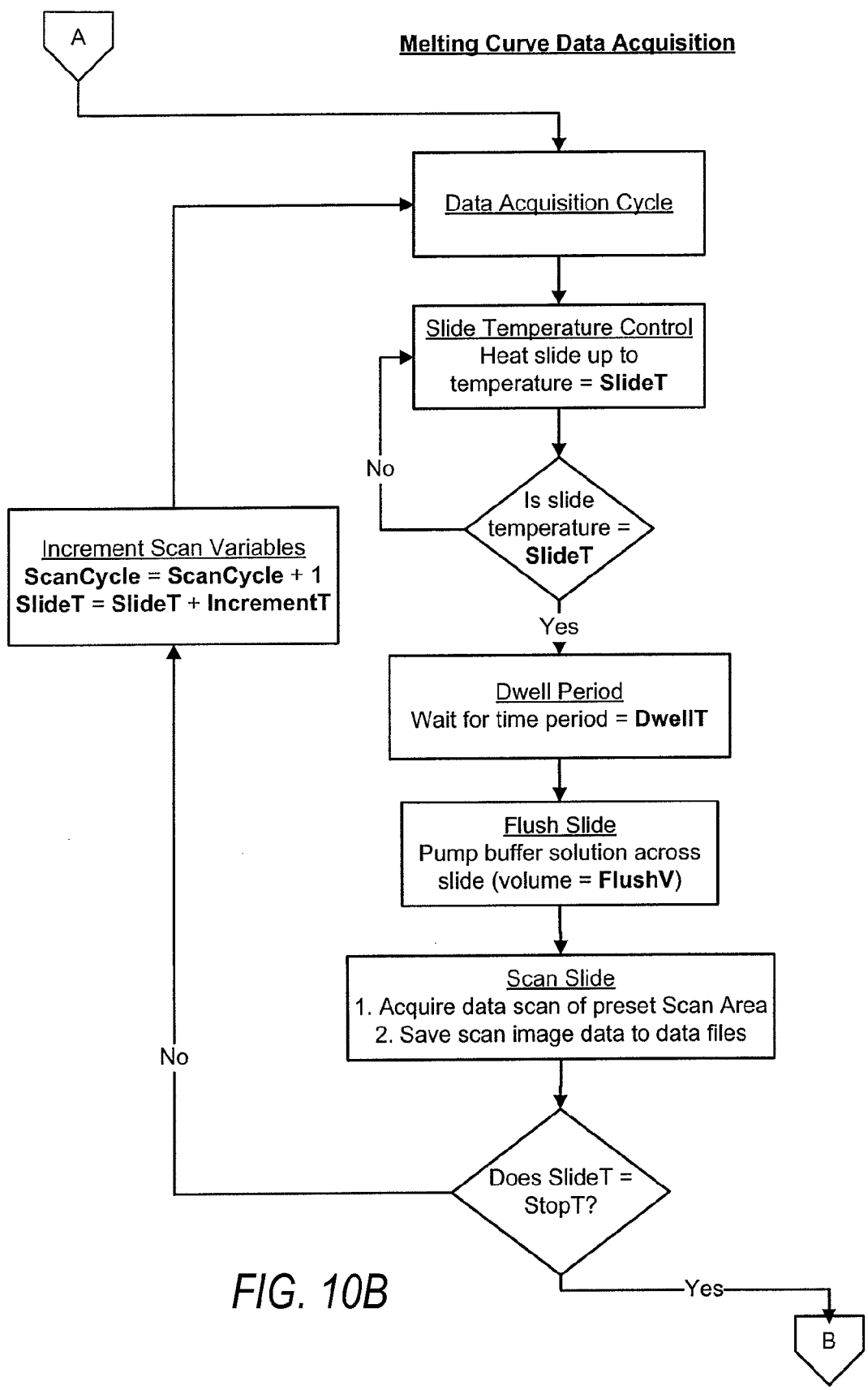
Figure 10C:
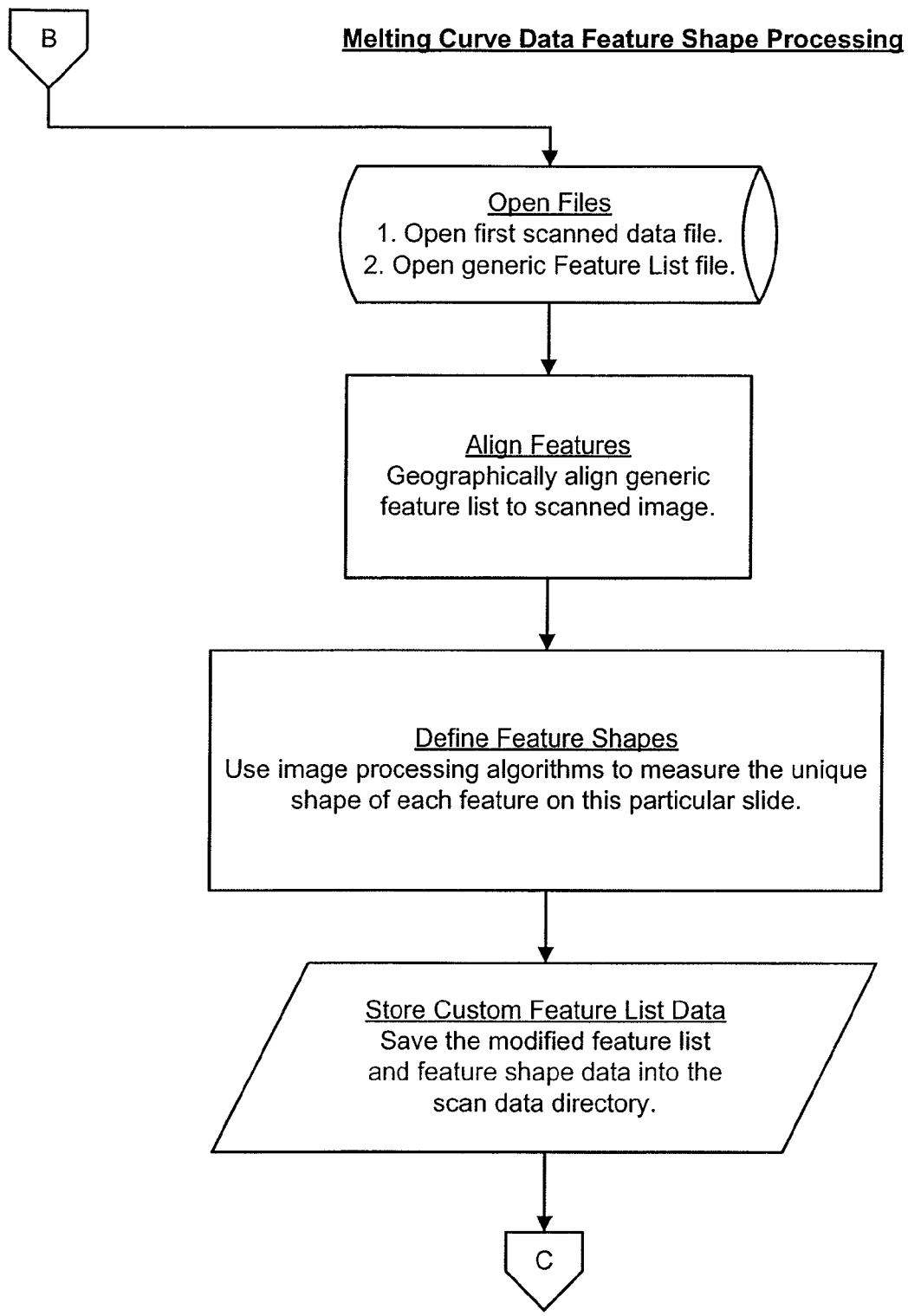
Figure 10D:
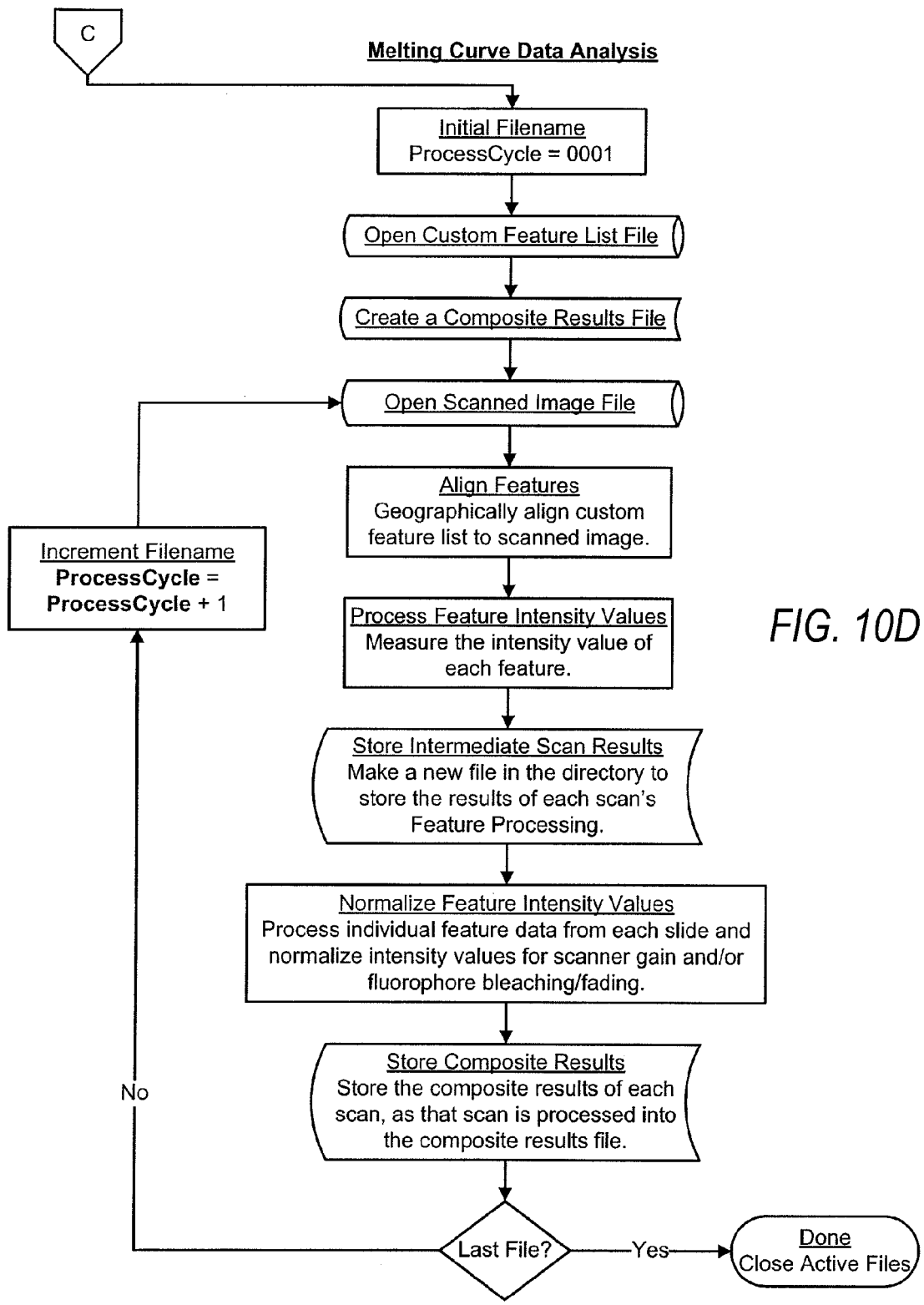

As the temperature of the microarray spots change the intensity changes, as the temperature increases the intensity decreases. To compensate for the change in intensity the gain of the detection system can be changed proactively. As the temperature is increased the gain is increased one step per each temperature step. The gain is increased enough each temperature step to keep the average spot intensity at the middle of the range of the detection system. FIG. 9 shows an example of data using the fluorescence intensity data normalization method.

Fluorescence FRET, FLIM, or FCS Methods

Further improvements in the signal to noise ration can be obtained by using advanced fluorescence spectroscopy techniques such as FRET, FLIM, or FCS. Each of these techniques has the ability to distinguish target DNA which is bound to probe DNA from target DNA which is nearby but not bound to probe DNA. Also, these techniques can be used together or separate from each other.

FRET uses two fluorescent dyes known as FRET partners and can be used to indicate that two complementary strands of DNA are within or less than 10-15 nm of each other. The donor FRET partner is attached to one stand of DNA such as the probe DNA. When the donor dye becomes excited and transfers its energy to the acceptor dye present on the other complimentary target strand of DNA. Therefore, exciting the donor dye results in emissions from the acceptor dye. However, the acceptor stand must be within an optimal distance which is often 10-15 nm or less for this effect to occur. The detection of FRET is an indication that complementary stands of DNA are likely bound to each other and not melted apart. And vice versa, the reduction in FRET is an indication that complementary strands of DNA are moving apart. In practice, a ratio of the both fluorescence intensity from both FRET dye partners is used. For example if the FRET dyes combination is Cy3 and Cy5. The donor dye is Cy3 is attached to the probe DNA and target DNA is labeled with Cy5. Optimal Cy5 fluorescence is observed when target is bound to probe DNA and the ratio of Cy5 to Cy3 is high. As target melts apart from probe DNA, Cy5 levels decrease indicating that target DNA is being separated from probe DNA and that ratio of Cy5 to Cy3 becomes smaller.

FLIM measures the exponential decay rate of fluorescence rather than fluorescence intensity. Since the micro environment in which a fluorescent dye is present can affect the decay rate, FILM can be used to determine if a DNA strand is single stranded or double stranded based on differences in fluorescence lifetime. Once target DNA has bound probe DNA, the immediate environment around the fluorescent dye has changed and the fluorescence lifetime will change accordingly (e.g. several nano seconds or more) in comparison to unbound target DNA in solution. FLIM can used alone or together with the FRET technique to reduce noise in the microarray system.

Example of Fluidics Array Method: Gene Expression Profiling for a Two-Color Microarray If a cancer researcher wants to compare gene expression levels between a cancer cell line and normal untransformed cells of the same type, cells of each type are harvested, mRNA extracted, and cDNA synthesized with concurrent staining with either Cy3 or Cy5 fluorescent dyes.

Traditional microarray gene expression profiling would consists of mixing both cDNA samples into a slurry and performing a two color microarray by placing the mixture on the array with cover slip over the fluid mixture and allowing hybridization to occur. This is a competitive hybridization with cDNA present in greater amounts out competing cDNA from the other cell type for binding to array probe spots. The array is then washed, dried, and read in the traditional reading machine capable of two-color fluorescence acquisition. Gene expression levels are determined by measuring the fluorescence intensity of one dye color and comparing it to the intensity of the other dye color. Traditional microarrays are known for significant inaccuracies that can be as high as several fold and all interesting results must be validated using a more accurate low throughput method such as Real-Time PCR. The validation step adds significantly to the overall cost of the experiment.

In comparison, the hybridization procedure of a fluidics array method would be performed in an identical manner. However, instead of drying the array, the chip is left wet and placed in a microarray cassette with an optical window or cover slip over the printed array surface. This chip is read in the machine by progressively increasing the temperature and scanning the chip for fluorescence in two colors until all targets DNA has melted off the probe DNA. Because this is a fluidics array, temperature change and flushing mechanisms are performed by pumping temperature control buffer onto the array surface but under the cover slip with excess buffer and melted target DNA drained to a waste collection bottle. So, for each flush or pulse of buffer in the array, the chip is scanned for fluorescence intensity in repeated cycles.

For each probe, a graph of temperature change versus fluorescence intensity is produced. In contrast to traditional microarray methods, the fluidics array allows any junk DNA or noise to be eliminated from the final calculation by not measuring melting curves produced at lower temperatures. Accuracy will be increased enough to eliminate the need for validation tests. In general noise in the microarray system will cause differences in gene expression between samples to appear smaller than they accuracy are.

For example, if the true difference in gene expression is 2:1, excess noise would make this difference appear to be closer to 1:1. With the use of melting curve analysis, the temperature at which each sample has the greatest difference in gene expression in relation to the other sample is likely to be the most accurate reading. So using melting curve analyses will correct the differences in gene expression and make them closer to the true 2:1 ratio. Also, the presence of SNPs can be detected by observing melting curves that are a few degrees lower than the predicted temperatures. Leading array manufactures use up to 40 different probes to interrogate each SNP. Melting analysis can reduce the number of probes need to 4 or less per SNP increasing the throughput by 10 fold. The use of normalization procedures involving incrementally adjusting the gain may or may not be used. FRET, FILM, two-photon microscopy and or FCS (embodiment 3) can be used with this procedure if greater increases in accuracy and reductions in noise are needed. Furthermore, target DNA in the liquid waste can be reused by affinity purifying the nucleic acids. Also the array chip can be reused after the target DNA has been removed and the chip washed.

We claim:

1. An apparatus for conducting a melting curve analysis of nucleic acids on a microarray by exciting a predefined portion of the microarray with a light beam and detecting emissions of fluorescent light comprising:
   an illuminator assembly, including a
       light source configured to produce the light beam, the light beam comprising electromagnetic radiation having one or more wavelengths,
       a band pass filter configured to eliminate wavelengths close to the wavelength of fluorescent light emitted from the nucleic acids,
       a mirror configured to reflect the light beam and to allow the fluorescent light emission to pass through, and
       an objective lens configured to focus the light beam on a predefined portion of the microarray;
   an emissions detector including a light intensity adjustment assembly, wherein the emissions detector is configured to sense emissions of fluorescent light from the predefined portion of the microarray, wherein the light beam produced by the light source and the emissions of fluorescent light are configured for transmission along a coincident path, and wherein the light intensity adjustment assembly is configured to compensate for a change in intensity as a temperature of the predefined portion of the microarray changes;
   a fluid circulation system, including
       a microarray cassette assembly including
           a frame including
               an opening configured to receive a microarray slide, the opening having a spacer disposed about an inside perimeter,
               a fluid inlet port positioned on a first end of the frame between a first distal edge of the frame and the inside perimeter of the opening; and
               a fluid outlet port positioned on an opposing parallel end of the frame between a second distal edge of the frame and the inside perimeter of the opening,
           an optical window attached to the frame,
           a seal disposed on the frame opposite the optical window,
           wherein when a microarray slide is received within the opening, the spacer maintains the microarray slide separate from the optical window, the space between the microarray slide and the optical window defining a microarray chamber configured to allow the flow of temperature controlled fluid from the fluid inlet port to the fluid outlet port across the microarray slide, such that dissociated target DNA is removed from the microarray slide by the fluid during a temperature change;
       a pump configured to receive fluid from a fluid reservoir and to circulate the fluid through a fluid supply line coupled to a temperature control assembly, and
       a fluid return line coupled to the fluid outlet port,
       wherein the temperature control assembly includes
           a temperature controller,
           a heat plate,
           a heater at a first heat plate side,
           a heater block at a second heat plate side, and
           a fluid heater including a fluid delivery tube, wherein the fluid delivery tube is disposed within a channel formed in the heater block, the channel configured to circle along an inside perimeter of the heater block more than once, the fluid delivery tube configured to allow the flow of fluid from the fluid supply line to the fluid inlet port through the fluid delivery tube, the fluid heater configured to transfer thermal energy with the fluid, the fluid having an equal temperature to a temperature of the heater block at a fluid delivery tube outlet end coupled to the fluid inlet port,
       wherein the fluid heater is in fluid communication with at least one of the fluid supply line and the fluid return line,
       wherein the heater is configured for the transfer of thermal energy with the microarray chamber through the heat plate and heater block, and
       wherein the heater is configured for the transfer of thermal energy with the fluid circulation system through the heat plate and heater block; and
   wherein the light beam and the micro array are movable relative to each other.

2. The apparatus of claim 1, wherein the microarray is movable in a first direction and the light beam is movable in a second direction, the second direction being substantially perpendicular to the first direction.

3. The apparatus of claim 1, wherein the light beam is fixed and the microarray is movable in a first direction and wherein the microarray is also movable in a second direction, wherein the second direction is substantially perpendicular to the second direction.

4. The apparatus of claim 3 further including:
a frame movably attached to a base and configured to receive the microarray cassette,
a first frame positioner attached to the base and configured to directionally move the frame along a first axis, and
a second frame positioner attached to the base and configured to directionally move the frame along a second axis, the second axis being perpendicular to the first axis.

5. The apparatus of claim 1 wherein the emissions detector further comprises a dichroic filter positioned such that the fluorescent light emitted from the nucleic acids passes through the dichroic filter before entering the emissions detector.

6. The apparatus of claim 1 wherein the emissions detector is selected from the group consisting of a photomultiplier tube, an avalanche photodiode, a photo sensor, and a digital camera.

7. The apparatus of claim 1 wherein the temperature control assembly comprises an electrical heating element.

8. The apparatus of claim 1 wherein the heater comprises a thermoelectric Peltier device.

9. The apparatus of claim 1 further comprising a waste line in fluid communication with one of the fluid supply line and the fluid return line.

10. The apparatus of claim 9 further including a waste reservoir in fluid communication with the waste line configured to collect waste fluid from the fluid circulation system.

11. The apparatus of claim 1 wherein the fluid reservoir includes a preheater.

12. The apparatus of claim 1 wherein the fluid reservoir comprises a plurality of chambers configured to contain a plurality of distinct fluids for introduction to the fluid circulation system.

13. The apparatus of claim 12 further comprising a selector configured to introduce a specific fluid into the fluid circulation system from the plurality of distinct fluids.

14. A microarray cassette assembly for use in an apparatus for conducting a melting curve analysis of nucleic acids, the microarray cassette assembly comprising:
a frame, having an opening including an inside perimeter, the opening being configured to receive a microarray slide and a spacer disposed about an inside perimeter of the opening;
an optical window hingedly connected to the frame and disposed on one side of the opening;
a fluid inlet port positioned on a first end of the frame between a first distal edge of the frame and the inside perimeter of the opening,
a fluid outlet port positioned on an opposing parallel end of the frame between a second distal edge of the frame and the insider perimeter of the opening,
a seal attached to the frame opposite the optical window; and
a temperature control assembly including
a temperature controller,
a heat plate,
a heater at a first heat plate side,
a heater block at a second heat plate side, and
a fluid heater including a fluid delivery tube, wherein the fluid delivery tube is disposed within a channel formed in the heater block, the channel configured to circle along an inside perimeter of the heater block more than once, the fluid delivery tube configured to allow the flow of fluid from a fluid supply line to the fluid inlet port through the fluid delivery tube, the fluid heater configured to transfer thermal energy with the fluid, the fluid having an equal temperature to a temperature of the heater block at a fluid delivery tube outlet end coupled to the fluid inlet port,
wherein the spacer is configured such that when the microarray slide is disposed within the opening, the microarray slide is spaced apart from the optical window, the space between the microarray slide and the optical window defining a chamber,
wherein the heater is configured for the transfer of thermal energy with the chamber through the heat plate and heater block, and
wherein the chamber is configured to receive a temperature controlled fluid through the inlet port, the fluid having a flow that is distributed across the microarray slide, and discharged from the microarray chamber through the outlet port, such that dissociated target DNA is removed from the microarray slide by the fluid during a temperature change.

15. An apparatus for conducting a melting curve analysis of nucleic acids on a microarray by exciting a predefined portion of the microarray with a light beam and detecting emissions of fluorescent light comprising:
an illuminator assembly, including a light source configured to produce the light beam, the light beam comprising electromagnetic radiation having one or more wavelengths,
an emissions detector including a light intensity adjustment assembly, wherein the emissions detector is configured to sense emissions of fluorescent light from the predefined portion of the microarray, wherein the light beam produced by the light source and the emissions of fluorescent light are configured for transmission along a coincident path, and wherein the light intensity adjustment assembly is configured to compensate for a change in intensity as a temperature of the predefined portion of the microarray changes;
a fluid circulation system, including
a microarray cassette assembly defining a microarray chamber, the micro array cassette assembly including a fluid inlet port positioned on a first end of the cassette assembly and a fluid outlet port positioned on an opposing parallel end of the cassette assembly, the fluid inlet port and the fluid outlet port each set on the cassette assembly between an inner perimeter of the chamber and a distal edge of the cassette assembly, the chamber configured to receive a temperature controlled fluid through the fluid inlet port, the fluid having a flow distributed across a microarray slide, such that dissociated target DNA is removed from the microarray slide by the fluid during a temperature change,
a pump configured to receive the fluid from a fluid reservoir and to discharge the fluid through a fluid inlet line coupled to a temperature control assembly, and
a fluid outlet line coupled to the fluid outlet port,
wherein the temperature control assembly includes
a temperature controller,
a heat plate,
a heater at a first heat plate side,
a heater block at a second heat plate side, and
a fluid heater including a fluid delivery tube, wherein the fluid delivery tube is disposed within a channel formed in the heater block, the channel configured to circle along an inside perimeter of the heater block more than once, the fluid delivery tube configured to allow the flow of fluid from the fluid inlet line to the fluid inlet port through the fluid delivery tube, the fluid heater configured to transfer thermal energy with the fluid, the fluid having an equal temperature to a temperature of the heater block at a fluid delivery tube outlet end coupled to the fluid inlet port, wherein the heater is configured for the transfer of thermal energy with the microarray chamber through the heat plate and heater block, wherein the heater is configured for the transfer of thermal energy with the fluid circulation system through the heat plate and heater block, wherein the temperature controller is configured to regulate the temperature of a fluid within the fluid circulation system, the temperature control assembly including at least one of a fluid heater in fluid communication with the fluid inlet line, a fluid heater in fluid communication with the fluid outlet line, and a fluid reservoir pre-heater and;

a microarray positioner, including a microarray cassette support movably attached to a base and configured to receive the microarray cassette, a first support positioner attached to the base and configured to directionally move the microarray cassette support along a first axis, and a second support positioner attached to the base and configured to directionally move the microarray cassette support along a second axis, the second axis being perpendicular to the first axis.

* * * * *